US006494085B2

(12) United States Patent
Wakefield et al.

(10) Patent No.: US 6,494,085 B2
(45) Date of Patent: *Dec. 17, 2002

(54) METHOD AND SYSTEM FOR DETECTING THERMAL ASPERITY ON DISCS USED IN A DISC DRIVE

(75) Inventors: Shawn Alan Wakefield, Norman, OK (US); Robert Matousek, Oklahoma City, OK (US)

(73) Assignee: Seagate Technology LLC, Scotts Valley, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/395,915

(22) Filed: Sep. 14, 1999

(65) Prior Publication Data

US 2002/0056313 A1 May 16, 2002

Related U.S. Application Data

(60) Provisional application No. 60/100,283, filed on Sep. 14, 1998.

(51) Int. Cl.[7] .............................. G01B 7/034; G11B 5/09
(52) U.S. Cl. .............................. 73/105; 73/104; 360/25; 360/46
(58) Field of Search .................. 73/104, 105, 12.01, 73/12.09; 360/25, 46

(56) References Cited

U.S. PATENT DOCUMENTS

| 5,808,184 | A |   | 9/1998 | Boutaghou et al. ............ 73/105 |
|---|---|---|---|---|
| 5,825,181 | A |   | 10/1998 | Schaenzer et al. .......... 324/212 |
| 5,828,181 | A |   | 10/1998 | Okuda ..................... 315/169.3 |
| 5,872,311 | A |   | 2/1999 | Schaenzer et al. ............. 73/105 |
| 5,898,532 | A |   | 4/1999 | Du et al. ....................... 360/46 |
| 5,952,563 | A | * | 9/1999 | Shiriaki ....................... 73/105 |
| 5,956,197 | A | * | 9/1999 | Le et al. ....................... 360/67 |
| 6,038,091 | A | * | 3/2000 | Reed et al. ................... 360/46 |
| 6,049,763 | A | * | 4/2000 | Christiansen et al. ....... 702/133 |
| 6,091,560 | A | * | 7/2000 | Du ............................... 360/53 |
| 6,104,557 | A | * | 8/2000 | Kasai et al. ................. 360/46 |
| 6,178,053 | B1 | * | 1/2001 | Narita ......................... 360/25 |

* cited by examiner

*Primary Examiner*—Hezron Williams
*Assistant Examiner*—Michael Cygan
(74) *Attorney, Agent, or Firm*—Merchant & Gould P.C.

(57) ABSTRACT

A method and system for providing adaptive threshold levels for detecting thermal asperities where a unique threshold level is determined for each head. In addition, a unique threshold level is also set for each head at various locations on a disc. In particular, a threshold level for a first head in a first track is determined wherein the threshold level is initially set at a minimum threshold level and is subsequently increased by a threshold level increment until a detection is not made. These steps can be repeated for the first head in a second track and a second head in a first and second track. A memory saves the determined threshold levels.

18 Claims, 3 Drawing Sheets

FIG. 3

| ZONE | TRANSDUCER | | | |
|---|---|---|---|---|
| | 1 | 2 | 3 | ...n |
| 1 | $TA_{11}$ | $TA_{21}$ | $TA_{31}$ | $TA_{n1}$ |
| 2 | $TA_{12}$ | $TA_{22}$ | $TA_{32}$ | $TA_{n2}$ |
| . | . | . | . | . |
| . | . | . | . | . |
| . | . | . | . | . |
| n | $TA_{1n}$ | $TA_{2n}$ | $TA_{3n}$ | $TA_{nn}$ |

METHOD AND SYSTEM FOR DETECTING THERMAL ASPERITY ON DISCS USED IN A DISC DRIVE

RELATED APPLICATION

This application claims the benefit of provisional application Ser. No. 60/100,283 entitled "Technique for Thermal Asperity Detection Using Adaptive Thresholds" filed on Sep. 14, 1998.

FIELD OF THE INVENTION

The present invention relates generally to a method and system for detecting thermal asperities on discs used in disc drives. More particularly, the present invention relates to a method and system for detecting thermal asperities that utilizes adaptive threshold levels that vary from transducer to transducer and from position to position along a disc.

BACKGROUND OF THE INVENTION

In disc drive data storage devices, digital data is written to and read from a thin layer of magnetizable material on a surface of one or more rotating discs. Write and read operations are performed through a transducer which is carried on a slider body. The slider and transducer are sometimes collectively referred to as a head, and typically a single head is associated with each disc surface. When the transducer is a magnetoresistive (MR) type sensor, the combination of the slider and the transducer are frequently referred to as an MR head. The heads are selectively moved under the control of electronic circuitry to any one of a plurality of circular, concentric data tracks on the disc surface by an actuator device. Each slider body includes an air bearing surface and, as the disc rotates, the disc drags air beneath the air bearing surface which develops a lifting force that causes the head to lift and fly several microinches above the disc surface.

In operation, the head can come into contact with asperities on the surface of the disc while the head flies above the surface of the disc. Potentially, this undesirable contact can cause data written to a particular location on the disc to be lost. Immediately after contact with an asperity, the heat generated by the contact changes the resistive properties of the MR sensor. As a result, the corresponding signal read by the MR head is distorted by a voltage spike and subsequent decay, sometimes causing the data stored near the asperity to be unrecoverable. The voltage spike in the read signal is frequently referred to as "thermal asperity," while the defect on the disc is referred to as an "asperity". However, since one is indicative of the other, the two terms are frequently used interchangeably.

Disc asperities which are located in the factory during a defect scanning process can be recorded in a disc drive's primary defect list so that the drive does not store data at those locations. Currently the defect scanning process is carried out using a thermal asperity sensor mounted on an air bearing surface of a slider. The air bearing surface is positioned a small distance from the surface of a rotating disc to be tested. The thermal asperity sensor can move along the radius of the disc to detect thermal asperities from the outer diameter to the inner diameter of the disc. The thermal asperity sensor is operatively coupled to a testing apparatus. The testing apparatus has a preamplifier with a thermal asperity detection function. A threshold level is set in the preamplifier. The threshold level is fixed for all heads in all drives. If a reading from the sensor is greater than the fixed threshold level, it is saved as a detected thermal asperity.

The prior art method of using a fixed threshold level has several disadvantages. Primarily head amplitudes vary not only from head to head but also in each head as it is moved from an outer diameter of a disc to the disc's inner diameter. Also, the level of the amplitude detected by the preamplifier is affected by the preamp's gain and process variation. In addition, the slope and range of the programmable thermal asperity threshold varies from one vendor's preamplifier to another vendor's preamplifier.

Furthermore, if the threshold level is not properly set, false detections may occur. For example, noise may be improperly classified as a thermal asperity and logged as a defect. As a result, data will not be written to that portion of the disc. This has the disadvantage that usable areas of a disc are not used. This is particularly disadvantageous if the number of false detects is large.

Accordingly, there is a continual need for improvements in the art whereby the detection of thermal asperities can be optimized and false detects can be reduced. In addition, there is a need for a method and system of thermal asperity detection that takes into account variations in vendor parts, variations in transducers as well as disc location variations.

The present invention provides a solution to the above and other problems and offers the above and other advantages over the prior art.

SUMMARY OF THE INVENTION

The present invention relates to a method and system which solves the above-mentioned problems and offers the above mentioned advantages. More particularly, the present invention relates to method of adaptively setting a threshold level for a disc drive system to test for thermal asperities. In one embodiment, the method includes the steps of determining a first threshold level for a first transducer in a first track and determining a second threshold level for the first head in a second track. In another embodiment, the method includes the steps of determining a first threshold level for a first head in a first track and determining a second threshold level for a second head in the first track.

In still another embodiment, the method includes the steps of determining a threshold level for a first head in a first track, determining a threshold level for the first head in a second track and saving the threshold levels for the first head. The steps of determining the threshold level for the first head include initially setting the threshold level at a minimum threshold level, determining whether a detection is made at that threshold level. If a detection is made at that level, increasing the threshold level by an increment and determining whether a detection is made at the incremented threshold level. These steps are repeated until a threshold level is reached where a detection is not made in order to not detect noise.

In another embodiment of the invention, there is provided a system for adaptively setting a threshold level for a disc drive to test for thermal asperities. The system includes a programmable controller that is programmed to determine a threshold level for a first transducer in a first track and a second track. The threshold level is initially set at a minimum threshold level and is subsequently increased until a detection is not made. The threshold levels for the first transducer are saved in a memory.

Accordingly, the present invention provides a method and system of detecting thermal asperities while reducing the likelihood of false detects thereby improving the amount of the disc that is usable.

Another advantage of the present invention is that it provides a more accurate asperity defect mapping. In addition, it eliminates the inflexibility of using a fixed threshold for all heads at all positions along disc.

These and various other features as well as advantages which characterize the present invention will be apparent upon reading of the following detailed description and review of the associated drawings.

BRIEF DESCRIPTION OF THE DRAWINGS

FIG. 3 is an example of the test data saved according to a preferred embodiment.

DETAILED DESCRIPTION

Figure 1:
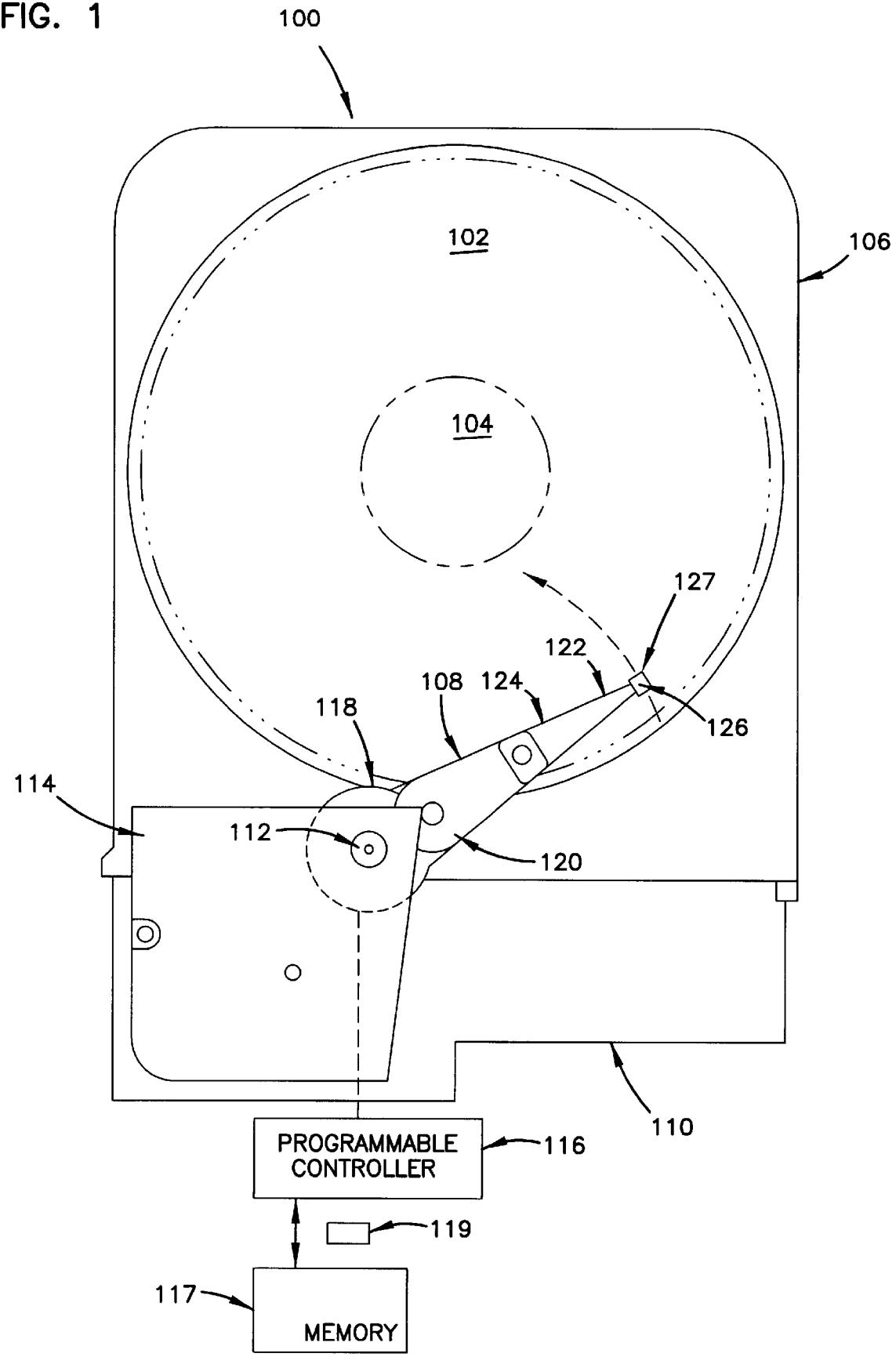
FIG. 1 is a top view of a thermal asperity scanning platform according to a preferred embodiment of the present invention.

FIG. 1 is a top view of a thermal asperity scanning platform 100, according to a preferred embodiment of the present invention. The platform 100 includes a spindle 104 which defines an axis about which a plurality of magnetic discs 102 are mounted for rotational movement within housing 106. Platform 100 also includes a stacked slider system 108 mounted to a base plate 110 of the housing 106. The stacked slider system 108 is pivotally movable relative to disc 102 about axis 112. A cover 114 covers a portion of stacked slider system 108. Programmable controller 116 is operatively coupled to the stacked slider system 108. In a preferred embodiment, programmable controller 116 is either mountable within platform 100 or is located outside of the platform 100 with suitable connection to stacked slider system 108. A memory 117 is operatively coupled to the programmable controller 116. Data 119 concerning threshold levels determined in the scanning procedure are saved in memory 117. A detailed description of data 119 will be given hereinafter. Alternatively, memory 117 can be located in the programmable controller 116.

In a preferred embodiment, stacked slider system 108 includes an arm assembly 118, a plurality of rigid support members 120, and a plurality of head gimbal assemblies 122 coupled to the arm assembly 118. Each head gimbal assembly 122 includes a load beam or flexure arm 124 coupled to rigid member 120, and a slider 126 coupled by a gimbal (not shown) to load beam 124. Each slider 126 supports a thermal asperity sensor 127 for detecting thermal asperities on a disc 102.

Figure 2:
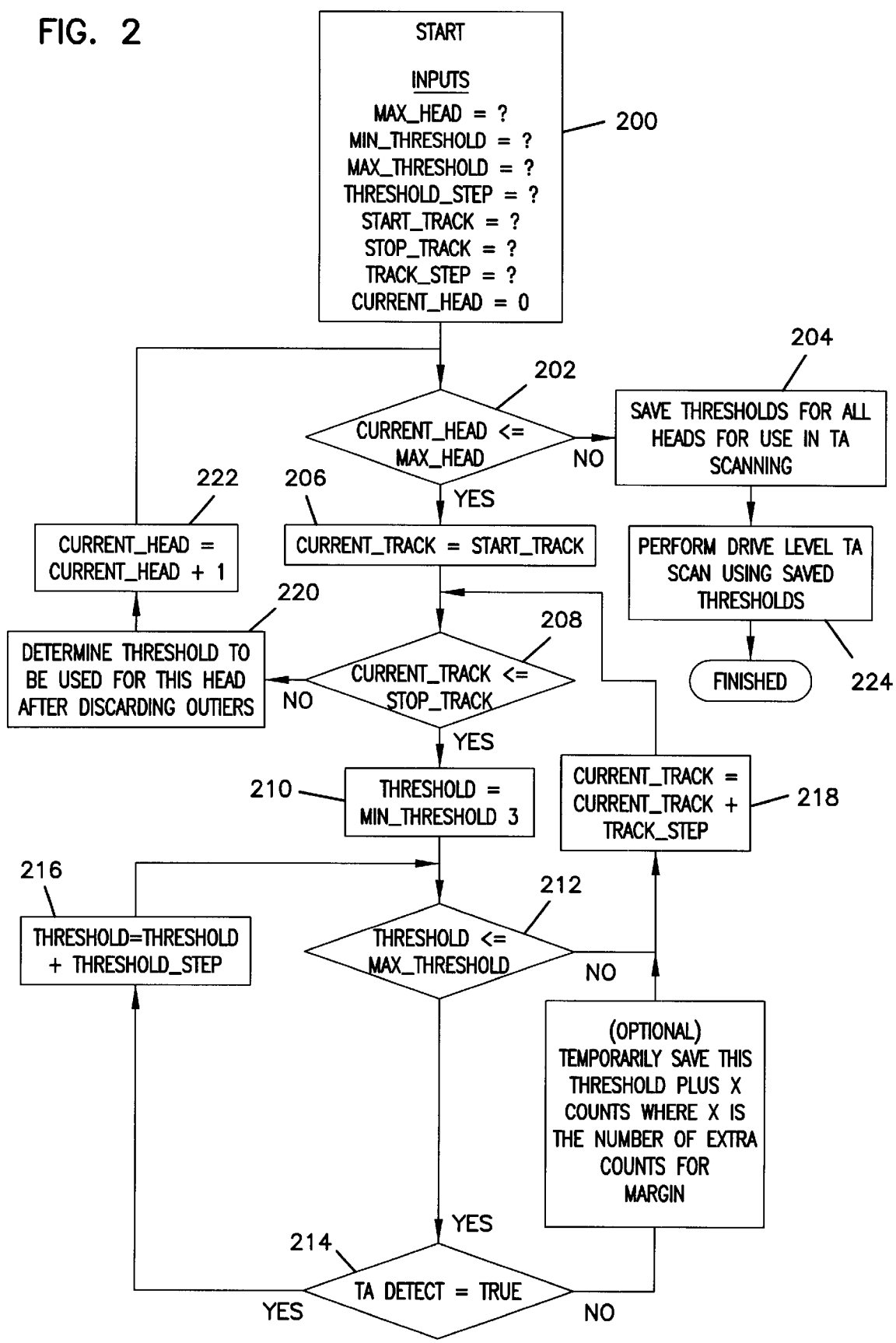
FIG. 2 is a flow chart of the operation of the test circuitry.

Operation of the test circuitry will now be described with reference to the flow chart of FIG. 2. A plurality of discs are mounted on the test platform. At block 200, a plurality of parameters are defined by the operator of the test circuitry. These parameters can be input through a keyboard coupled to the programmable controller 116, for example. Alternatively, the inputs can be downloaded from a memory or storage media such as a disc. In particular, the following inputs are defined.

| Parameter | Definition |
|---|---|
| Max_head = ? | the total number of heads on which are located sensors located on the test platform |
| Min_threshold = ? | a minimum threshold level |
| Max_threshold = ? | a maximum threshold level |
| Threshold_step = ? | a threshold increment value |
| Start_track = ? | at what location on a disc should testing begin |
| Stop_track = ? | at what location on a disc should testing stop |
| Track_step = ? | a location increment value |
| Current_head = 0 | the head (i.e., sensor) currently being tested. |

At step 202 it is determined whether the head to be tested exceeds the last head to be tested. If it does not, meaning that the last head has been tested, control is passed to step 204 which will be described in detail hereinafter. Since the "Current_Head" parameter was defined to be zero in step 200, control is passed to step 206 where the track to be tested is set to the "Start_Track" parameter defined in step 200. At step 208 it is determined whether the track to be tested exceeds the last track to be tested. If it does not, control is passed to step 210 where a threshold level is set at the minimum threshold parameter defined in step 200. At step 212 it is determined whether the threshold level exceeds the maximum threshold level defined in step 200. Since this is the first pass through the loop, the threshold level will not exceed the maximum threshold level defined in step 200. At step 214, it is determined whether a reading from the thermal asperity sensor crosses the threshold level set in step 210. In a preferred embodiment, the minimum threshold level is set very low so that a detection most likely will be made. If this is the case, then control is passed to step 216 where the threshold level is increased by the increment threshold level parameter defined in step 200 and control is returned to step 212. The loop defined by steps 212, 214, 216 in essence raises the threshold level until no detection is made at step 214. By performing this loop, the threshold level is set at a point where noise is not being falsely detected as a thermal asperity. Once a threshold level is reached where no detection is made at step 214, or if the threshold level is incremented to a level where it exceeds the maximum level as defined at step 212, control is passed to step 218 where the track being tested is incremented by the location increment value defined in step 200. Control is then returned to step 208 where it is determined if the track being tested exceeds the stop track parameter defined in step 200. If it does not, testing is continued as defined in steps 210–218 for the new track. If it is determined that the last track has been tested, control is passed to step 220 where it is determined which threshold levels are to be retained and which threshold levels are to be discarded. Step 220 is optional and need not be performed. Then at step 222, the next head to be tested is set and control is returned to step 202 and the testing as described is performed for the next head. If it is determined at step 202 that the last head has been tested, control is passed to step 204 where all of the threshold levels not discarded in step 220 are saved for use in testing discs. These saved threshold levels are then used to perform a thermal asperity scan on discs at step 224. Optionally, the save thresholds may be a few counts higher than the minimum in order to add a margin. While the scan performed in step 224 is shown as directly following step 204, it is to be understood that the scan at step 224 can be performed at a later time and need not directly follow step 204.

The test data saved in step 204 is shown in FIG. 1 as data 119 sent to memory 117. FIG. 3 is an example of the test data 119 saved in step 204 according to a preferred embodiment of the present invention.

From the data shown in FIG. 3 it can be seen that for each head there is a unique threshold level associated therewith. Moreover, for various locations along a disc there is a unique threshold level associated therewith for each head. While the term "track" has been used to indicate location, a track as defined herein and with reference to FIGS. 2 and 3 can refer to a plurality of tracks, i.e., a zone.

In summary, the present invention is directed to a method of adaptively setting a threshold level for disc drive system to test for thermal asperities. In one embodiment, the method includes the steps of determining a first threshold level for a first transducer in a first track and determining a second threshold level for the first head in a second track. In another embodiment, the method includes the steps of determining a first threshold level for a first head in a first track and determining a second threshold level for a second head in the first track.

In still another embodiment, the method includes the steps of determining a threshold level for a first head in a first track, determining a threshold level for the first head in a second track and saving the threshold levels for the first head (204). The steps of determining the threshold level for the first head include initially setting the threshold level at a minimum threshold level (210), determining whether a detection is made at that threshold level (214). If a detection is made at that level increasing the threshold level by an increment (216) and determining whether a detection is made at that threshold levels (214). These steps are repeated until a threshold level is reached where a detection is not made.

In another embodiment of the invention, there is provided a system for adaptively setting a threshold level for a disc drive to test for thermal asperities. The system includes a programmable controller (116) that is programmed to determine a threshold level for a first transducer in a first track and a second track. The threshold level is initially set at a minimum threshold level (210) and is subsequently increased (216) until a detection is not made (214). The threshold levels for the first transducer are saved in a memory (204).

It will be clear that the present invention is well adapted to attain the ends and advantages mentioned as well as those inherent therein. While a presently preferred embodiment has been described for purposes of this disclosure, numerous changes may be made which will readily suggest themselves to those skilled in the art and which are encompassed in the spirit of the invention disclosed and as defined in the appended claims.

What is claimed is:

1. A method of adaptively testing for thermal asperities in a disc drive, the method comprising steps of:
  (a) determining a first threshold level, wherein the first threshold level is initially set at a minimum threshold level and is subsequently increased by a threshold level increment until a noise level detection is not made, for a first head in a first track; and
  (b) determining a second threshold level, wherein the second threshold level is initially set at a minimum threshold level and is subsequently increased by a threshold level increment until a noise level detection is not made, for the first head in a second track.

2. The method of claim 1 further comprising step (c) of determining a first threshold level for a second head in the first track.

3. A method of adaptively setting a threshold level for a disc drive system to test for thermal asperities, the method comprising steps of:
  (a) determining a first threshold level for a first head in a first track, wherein the first threshold level is initially set at a minimum threshold level and is subsequently increased by a threshold increment until a noise level detection is not made; and
  (b) determining a second threshold for a second head in the first track, wherein the second threshold level is initially set at a minimum threshold level and is subsequently increased by a threshold increment until a noise level detection is not made.

4. The method of claim 3 further comprising step (c) of determining second threshold level for the first head in the second track.

5. A method of adaptively testing for thermal asperities in a disc drive, the method comprising steps of:
  (a) determining a threshold level for a first head in a first track wherein the threshold level is initially set at a minimum threshold level, the step (a) of determining a threshold level comprising the steps of:
    (a)(i) determining whether a noise level detection is made at the threshold level;
    (a)(ii) if the noise level detection is made in step (a)(i), increasing threshold level by a threshold increment and repeating step (a)(i);
    (a)(iii) repeating steps (a)(i)–(a)(ii) until it is determined that the noise level detection is not made in step (a)(i);
  (b) repeating step (a) for the first head in a second track; and
  (c) saving the threshold levels determined in steps (a)–(b) for the first head.

6. The method of claim 5 further comprising step (d) of repeating steps (a)–(c) for a second head and (e) saving the threshold levels determined in step (d).

7. The method of claim 5 further comprising step (d) of repeating steps (a)–(c) for a plurality of heads.

8. The method of claim 5 further comprising step (d) of performing a drive level thermal asperity scan of a disc using the threshold levels saved in step (c).

9. The method of claim 5 further comprising step (d) of discarding any outlier threshold level determined in step (c).

10. The method of claim 5 wherein the step (a)(ii) includes a step (a)(ii)(a) of determining whether the threshold level is greater than a maximum threshold level and if it is, bypassing step (a)(iii) and proceeding directly to step (b).

11. The method of claim 5 further comprising step (c) of repeating step (b) for a plurality of subsequent tracks until it is determined that a last track has been tested.

12. The method of claim 5 wherein the step (a)(i) comprises determining if an output of the first transducer is greater than the threshold level.

13. A system for adaptively testing for thermal asperities in a disc drive, the system comprising:
  (a) a programmable controller operatively coupled to an input of plurality of variables including a first track, a second track, and minimum threshold and a threshold increment, the programmable controller programmable controller programmed to perform the following steps:
    (a)(i) determine a threshold level for a first head in a first track, wherein the threshold level is initially set at the minimum threshold level and is subsequently increased by the threshold level increment until a noise level detection is not made and
    (a)(ii) repeating step (a)(i) for the first head in a second track; and
  (b) a memory operatively coupled to the programmable controller for saving the threshold levels determined in step (a) for the first head.

14. The system of claim 13 further comprising means for inputting the plurality of variables wherein the means comprises a keyboard.

15. The system claim 13 wherein the programmable controller is programmed to perform steps (a)(i)–(a)(ii) for a second head.

16. A system for adaptively testing for thermal asperities in a disc drive, the system comprising:
   (a) means for controlling operatively coupled to an input of a plurality of variables including a first track, a second track, a minimum threshold and a threshold increment, wherein the means for controlling is programmed to perform the following steps:
      (a)(i) determine a threshold level for a first head in a first track, wherein the threshold level is initially set at the minimum threshold level and is subsequently increased by the threshold level increment until a noise level detection is not made and
      (a)(ii) repeating step (a)(i) for the first head in a second track; and
   (b) a memory for saving the thresholds determined in step (a) for the first head.

17. The system of claim 16 wherein the means for controlling is a programmable controller.

18. The system of claim 16 wherein the means for controlling additionally performs steps (a)(i)–(a)(ii) for a second head.

* * * * *